(12) United States Patent
Yang et al.

(10) Patent No.: US 9,689,865 B2
(45) Date of Patent: Jun. 27, 2017

(54) PERSONAL HYGIENE ITEM

(71) Applicant: National Tsing Hua University, Hsinchu (TW)

(72) Inventors: Chung-Yao Yang, Hsinchu (TW); Szu-Ting Lin, Hsinchu (TW); Jer-Liang Yeh, Hsinchu (TW); Chao-Min Cheng, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 130 days.

(21) Appl. No.: 14/665,566

(22) Filed: Mar. 23, 2015

(65) Prior Publication Data

US 2016/0106348 A1 Apr. 21, 2016

(30) Foreign Application Priority Data

Oct. 16, 2014 (TW) .............................. 103135896 A

(51) Int. Cl.
*G01N 21/75* (2006.01)
*G01N 33/52* (2006.01)
*A61L 15/42* (2006.01)
*A61L 15/56* (2006.01)

(52) U.S. Cl.
CPC ............ *G01N 33/528* (2013.01); *A61L 15/42* (2013.01); *A61L 15/56* (2013.01)

(58) Field of Classification Search
CPC ........ G01N 33/528; A61L 15/56; A61L 15/42
See application file for complete search history.

(56) References Cited

U.S. PATENT DOCUMENTS

| 6,203,496 B1 | 3/2001 | Gael et al. |
| 6,682,893 B2 | 1/2004 | Taylor et al. |
| 2004/0133090 A1 | 7/2004 | Dostoinov et al. |
| 2006/0229578 A1* | 10/2006 | Roe ........................ A61F 13/42 604/361 |
| 2009/0082745 A1 | 3/2009 | Ying et al. |

FOREIGN PATENT DOCUMENTS

| TW | I334345 B | 12/2010 |
| TW | M456182 U | 7/2013 |

* cited by examiner

*Primary Examiner* — Dennis M White
(74) *Attorney, Agent, or Firm* — Patterson + Sheridan, LLP

(57) ABSTRACT

The present invention provides a personal hygiene item. In simple terms, one of the main features of the present invention is to provide a low-cost personal hygiene item capable of providing a multi-component detection function. The personal hygiene item of the present invention mainly comprises a first material layer and a second material layer. The first material layer is made of hydrophobic material, and the second material layer is disposed thereon. Also, the second material layer comprises a discolored portion. In actual practice, a fluid under test contacts with the corresponding discolored portions via the hydrophobic layer of second material layer for a color changing reaction. Meanwhile, since the hydrophilic performance of the discolored portion is better than the hydrophilic performance of the hydrophilic layer, the back permeation of the fluid under test can herein be prevented.

18 Claims, 4 Drawing Sheets

PERSONAL HYGIENE ITEM

CROSS REFERENCE TO RELATED APPLICATION

This application claims priority to Taiwan Patent Document No. 103135896, filed on Oct. 16, 2014 with the Taiwan Patent Office, which is incorporated by reference in its entirety.

BACKGROUND OF THE INVENTION

1. Field of the Invention

The present invention discloses a personal hygiene item; and more particularly, the present invention discloses a personal hygiene item which has chemical examination function and is able to prevent the testing area of the present invention to contact with the skin of the user directly.

2. Description of the Prior Art

In the past, personal hygiene items which have fluid examination function mostly use paper to absorb the fluid testing material uniformly to serve as test paper. Then, the test paper is placed on the inner surface of the personal hygiene items for receiving the fluid of the user directly for color changing reaction. In practical application, the testing material of the test paper reacts with the predetermined constituent of the fluid under test and then changes color itself, which allows the user to know whether the fluid under test comprises the predetermined constituent or not for examination.

Take the U.S. Pat. No. 6,203,496 for example. This patent discloses a diaper, composed of a permeable layer, as absorption layer, and an impermeable layer. A chemical reagent is set for sensing the matter comprised in the urine by color change. The chemical reagent is directly dropped into the absorption layer to react with chemical matters comprised in the urine. When there is only a single reagent comprised, the effect of the application is less influenced. But, if the producer wants to drop various kinds of reagents into the absorption layer of the diaper at the same time, different kinds of reagents will be mixed due to capillarity, and then the reagents will lose efficacy.

Additionally, as shown in the Taiwan patent publication No. M456182, the patent discloses a method for examining the pH value of the urine by directly spreading the acid-base indicator on the inner surface of the impermeable outer layer of the diaper. Similarly, this patent utilizes the absorption layer to absorb the reagent for examination, and induces the same problem which can not support different kinds of reagents. To avoid the problems mentioned above, nowadays, silicon chips or other semiconductor materials are integrated in diapers to provide examination function of various constituents as well. But the manufacture process is complex and the cost is high, so this method is not common.

More particularly, nowadays, there is no art that can effectively produce a personal hygiene item having various kinds of testing materials with low cost. Therefore, the application is limited and fails to be promoted and applied.

The statement mentioned above is the current state of art of the personal hygiene item which has the function of chemical examination.

SUMMARY OF THE INVENTION

To solve the problem mentioned above, through testing and researching repeatedly, the inventor provides a personal hygiene item with simple fabrication, low cost, and the ability of examining various kinds of chemical matters at the same time. The structure of the personal hygiene item is disclosed in the present invention.

In brief, the personal hygiene item of the present invention mainly comprises a hydrophobic first material layer and a second material layer used to examine the property of the fluid under test. The second material layer comprises a hydrophilic portion, a first discolored portion, and a hydrophobic portion. The hydrophobic portion is covered over the surface of the hydrophilic portion. Meanwhile, the hydrophobic portion can have one or a plurality of perforations, wherein the perforations are independent and not connected with each others. When the hydrophobic portion is connected with the hydrophilic portion, the first testing area and the second testing area of the surface of the hydrophilic portion will be exposed through the perforations of the hydrophobic portion, and the first discolored portion and the second discolored portion having better hydrophilic performance than the hydrophilic portion can be disposed on the two testing areas at the same time respectively. The present invention utilizes the physical characteristic that the fluid will preferentially flow to the material having better hydrophilic performance, so the fluid under test will permeate into the first discolored portion through the hydrophilic portion, and then the first discolored portion is contacted with the fluid under test for color changing reaction. The operation theory of the second discolored portion is similar to the statement mentioned above, so the necessary details are not given again here.

By the design of the present invention, upon the urine permeates into each discolored portion, the urine after reaction will not preferentially flow back to the hydrophilic portion because the discolored portions have a better hydrophilic performance than the hydrophilic layer. Meanwhile, because the first discolored portion and the second discolored portion are isolated by at least one portion of the hydrophobic portion, cross contamination of the reagent and the fluid under test of each discolored portion can be avoided as well. Furthermore, because the disposition of each material can be integrated in the original manufacture process and the related design and art of the semiconductor is not needed to be applied, the present invention can be manufactured with lower cost, which overcomes the problems in the prior art for a long time.

To summarize the statement mentioned above, the priority of the present invention is to provide a personal hygiene item which is able to examine various kinds of constituents with low cost. In brief, the priority of the present invention is to provide a personal hygiene item which does not have cross contamination and is able to examine various kinds of chemical matters at the same time.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method is presented herein by way of exemplifications with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and is disclosed simply as an example of embodiments of the present invention. Additionally, if the description states that A and B are hydrophilic layer (material) and hydrophobic layer (material) respectively and does not clearly define the relationship between them, the terms of "hydrophilic" and "hydrophobic" are construed as "A has a better hydrophilic performance than B".

Figure 1A:
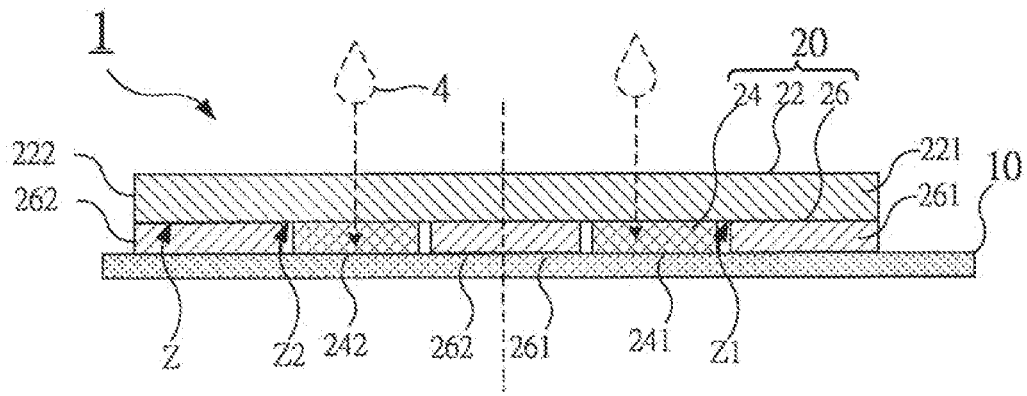
FIG. 1A and FIG. 1B show the schematic diagrams of the personal hygiene item according to the first embodiment with different angle of the present invention.
Figure 1B:
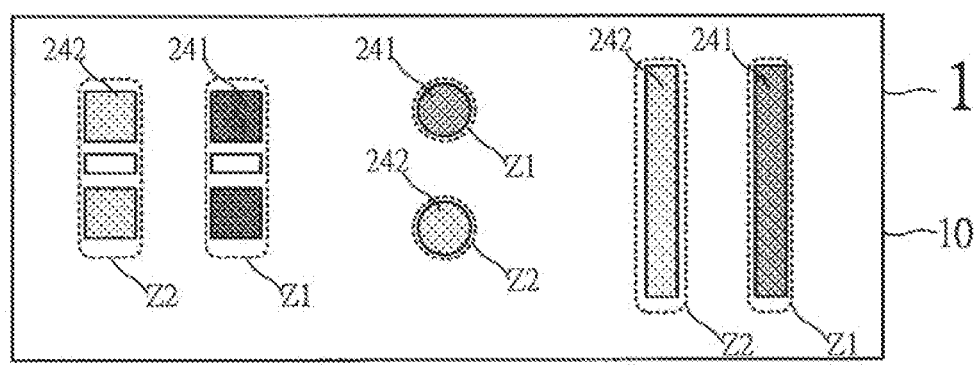

According to the statement mentioned above, the present invention provides a personal hygiene item, wherein the personal hygiene item can be a diaper, a sanitary napkin, a mask, or any disposable items which can be contacted with the skin or fluid of the user. Please refer to FIG. 1A and FIG. 1B. FIG. 1A and FIG. 1B show the schematic diagrams of the personal hygiene item according to the first embodiment with different angles of the present invention. More particularly, FIG. 1B shows the schematic diagram observed from another direction of the first material layer 10 relative to the second material layer 20.

As shown in each figure, in the best simplification, the personal hygiene item 1 of the present invention can only comprise a first material layer 10 and a second material layer 20 which is disposed on a surface of the first material layer 10.

In this embodiment, the first material layer 10 is preferentially made of a hydrophobic material, adapted to prevent the fluid under test 4 to pass through the first material layer 10 in liquid state, wherein at least one portion of the first material layer 10 is transparent or translucent. More particularly, in this embodiment, the first material layer can be a waterproof polymer gel film. The hydrophobic material mentioned above can be polymer fiber, flexible polymer film, or other kinds of materials processed by surface treatment to reduce the hydrophilic property thereof.

In another aspect, the second material layer 20 is disposed on inner surface of the first material layer 10, used to perform color changing reaction to the fluid under test 4 for examination. The fluid under test 4 is body fluids of human body, such as sweat, urine, saliva, menstrual blood, and fluids or gas outputted from the human body. In this embodiment, as shown in FIG. 1A, the second material layer 20 can comprise a hydrophilic portion 22, a discolored portion 24, and a hydrophobic portion 26.

The discolored portion 24 further can be divided into the first discolored portion 241 and the second discolored portion 242 according to the different positions thereof. The first discolored portion 241 and the second discolored portion 242 can comprise a same or different reacting matter respectively. Each reacting matter can be reacted with the corresponding chemical matter for color changing reaction. More particularly, the first discolored portion 241 or the second discolored portion 242 can be a fiber material dipped with reacting matter, such as cotton fabric or paper which has high hydrophilic property.

In another aspect, in this embodiment, the hydrophilic portion 22 and the hydrophobic portion 26 is referred to papers and the waterproof ink formed on the surface thereof respectively. But the present invention is not limited to the statement mentioned above. The hydrophilic portion 22 of the present invention also can be referred to any kinds of plate-shaped hydrophilic fiber material, such as fabric or hygroscopic polymer fiber. Besides the waterproof ink layer mentioned above, the hydrophobic portion 26 also can be the material like wax, hydrophobic polymer fiber or hydrophobic polymer film. And relative to the first discolored portion 241 and the second discolored portion 242, the hydrophilic portion 22 also can comprise a first hydrophilic portion 221 and a second hydrophilic portion 222 correspondingly. And the hydrophobic portion 26 can be divided into a first hydrophobic portion 261 and a second hydrophobic portion 262 correspondingly. In this embodiment, the first hydrophilic portion 221 and the second hydrophilic portion 222 are one-piece-formed and single-plate-shaped material, and so is hydrophobic portion 26.

Furthermore, the discolored portion 24 of the present invention can be presented by various kinds of ways, and the feasibility will be explained in the specification later.

After each material layer is explained, the following statement will explain the relationship of each element. In this embodiment, the hydrophilic portion 22 has a front surface and a corresponding back surface, wherein the front surface can comprise but not limit to a testing area Z, wherein the testing area Z can comprise a first testing area Z1 and a second testing area Z2; the first discolored portion 241 and the second discolored portion 242 can be disposed on the surface of the first testing portion Z1 and the second testing portion Z2 where is able to be contacted directly. It is needed to know that the testing area Z and the discolored portion 24 are not limited to the diagram shown in FIG. 1A and FIG. 1B. If needed, the present invention can father comprise a plurality of corresponding testing areas Z and discolored portions 24 in different shapes. It is needed to mention that when selecting the material for each discolored portion 24, the material having a better hydrophilic performance than the hydrophilic portion 22 should be selected to prevent permeating back.

More particularly, the user can allow the fluid under test 4 to get into and be contacted with the first discolored portion 241 via the hydrophilic portion 22 of the second material layer 20 for color changing reaction, and then the user can observe the change of the color of the first discolored portion 241 via the transparent or translucent portion of the first material layer 10. In another aspect, the present invention applies the physical characteristic that the fluid will preferentially flow to the material having better hydrophilic performance, so after the fluid under test 4 permeates into each discolored portion 24 through the hydrophilic portion 22, the fluid after reaction will not preferentially permeate hack into the hydrophilic portion 22 because each discolored portion 24 has better hydrophilic performance than the hydrophilic portion 22. By the method mentioned above, the cross contamination of each discolored portion 24 can be prevented.

In another aspect, the hydrophobic portion 26 is covered over the front surface of the hydrophilic portion 22. Meanwhile, in this embodiment, the hydrophobic portion 26 has a plurality of perforations, used to allow the first testing area Z1 and the second testing portion Z2 can be exposed from the first material layer 10 when the hydrophobic portion 26 is covered over the front surface of the hydrophilic portion 22. Meanwhile, the hydrophobic portion 26 is also disposed between the first testing area Z1 and the second testing area Z2, so the first testing area Z1 is isolated from the second testing area Z2, which further prevents the cross contamination of the first testing area Z1 and the second testing area Z2 to occur.

Figure 2:
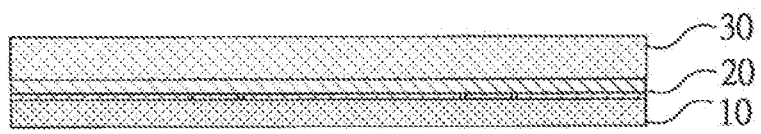
FIG. 2 shows the schematic diagram of the personal hygiene item according to the second embodiment with different angle of the present invention.

Please refer to FIG. 2. FIG. 2 shows the schematic diagram of the personal hygiene item according to the second embodiment with different angles of the present invention. As shown in FIG. 2, based on the embodiment in FIG. 1, the present invention can further comprise a third material layer 30, disposed on the other surface of the second material layer 20 relative to the first material layer 10 and connected with the second material layer 20, which means the second material layer 20 is disposed between the first material layer 10 and the third material layer 30. In this embodiment, the term of "connect" is construed as "contact". And in other conditions, the term of "connect" also can be referred as "simply connect".

Figure 3:
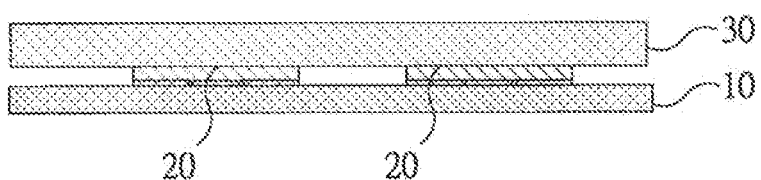
FIG. 3 to FIG. 13 show the schematic diagrams of the personal hygiene item according to the third to the thirteenth embodiment of the present invention.

In another aspect, the third material layer 30 is made of at least one hydrophobic material. The hydrophobic material mentioned above can be referred to a plate-shaped polymer fiber fabric, glue film, non-woven fabric with perforations, or any kinds of hydrophobic materials. Furthermore, the hydrophilic portion 22 and the hydrophobic portion 26 of the second material layer 20 can be one piece formed by single material selectively. And the present invention is not limited to the statement mentioned above. Please refer to FIG. 3. FIG. 3 shows the schematic diagrams of the personal hygiene item according to the third embodiment of the present invention. As shown in FIG. 3, if needed, the first hydrophilic portion 221 and the second hydrophilic portion 222 of the hydrophilic portion 22 can be disposed respectively, and so can the first hydrophobic portion 261 and the second hydrophobic portion 262 of the hydrophobic portion 26.

Figure 4:
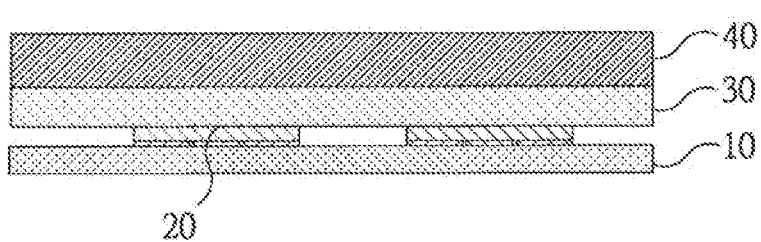

Additionally, please refer to FIG. 4. FIG. 4 shows the schematic diagrams of the personal hygiene item according to the forth embodiment of the present invention. As shown in the FIG. 4, based on the second embodiment, the present invention further comprises a forth material layer 40, which can be formed, disposed, or connected on the other surface of the third material layer 30 relative to the second material layer 20. The forth material layer 40 is a material layer used to absorb fluid. More particularly, in this embodiment, the forth material layer 40 can be made of a cotton fiber with ability of high absorption amount. When the personal hygiene item 1 is a diaper or a sanitary napkin, the forth material layer 40 can be used to absorb or store urine and menstrual blood respectively.

Figure 5:
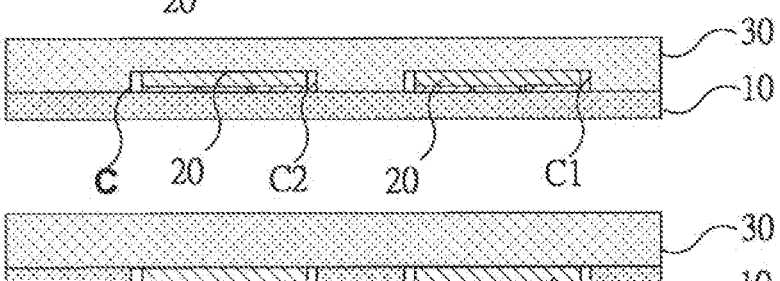
Figure 6:
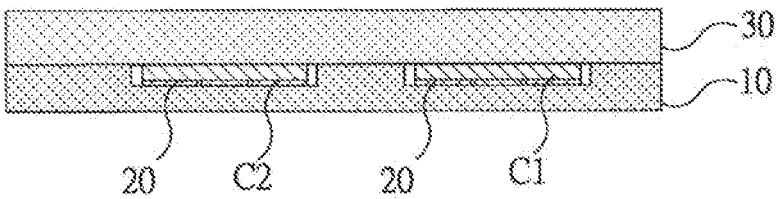

In another aspect, please refer to FIG. 5 and FIG. 6. FIG. 5 and FIG. 6 show the schematic diagrams of the personal hygiene item according to the fifth and the sixth embodiment of the present invention. As shown in the figures, based on the forth embodiment, the fifth and the sixth embodiment respectively demonstrate that a plurality of indentations C can be disposed on the first material layer 10 or the third material layer 30 respectively according to the second material layer 20. Each indentation C can further contain at least one part of the second material layer 20 or the whole second material layer 20 respectively or simultaneously. As shown in the figures, in this embodiment, one of the indentations, or the so-called first indentation C1, is adapted to contain the first hydrophilic portion 221, the first discolored portion 241, and the first hydrophobic portion 261. And the other indentation C, or the so-called second indentation C2, is adapted to contain the second hydrophilic portion 222, the second discolored portion 242, and the second hydrophobic portion 262.

Figure 7:
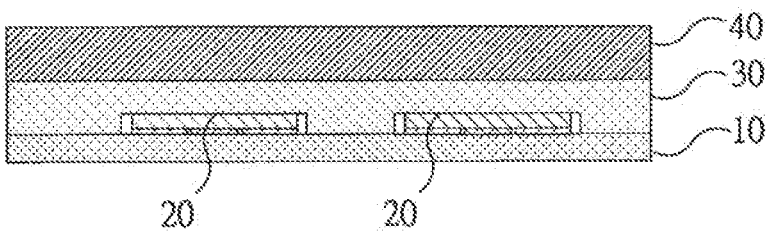

Please refer to FIG. 7. FIG. 7 shows the schematic diagrams of the personal hygiene item according to the seventh embodiment of the present invention. As shown in FIG. 7, based on FIG. 6, FIG. 7 further comprises a forth material layer 40, disposed on the other surface of the third material layer 30 relative to the second material layer 20 and connected with the third material layer 30, wherein the forth material layer 40 is made of a hydrophilic material, wherein the hydrophilic material has belter hydrophilic performance than the third material layer 30. More particularly, the forth material layer 40 is made of cotton fibers.

Figure 8:
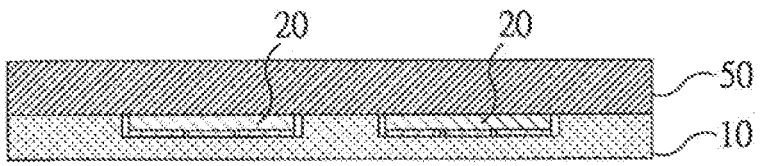

Additionally, please refer to FIG. 8. FIG. 8 shows the schematic diagrams of the personal hygiene item according to the eighth embodiment of the present invention. As shown in the figures, relative to the structure in FIG. 6, a fifth material layer 50 is disposed on the back of the second material layer 20 in FIG. 8. The fifth material layer 50 is disposed on the other surface of the second material layer 20 relative to the first material layer 10 and connected with at least one part of the second material layer 20. Meanwhile, the fifth material layer 50 is a hydrophilic layer. More particularly, in this embodiment, the fifth material layer 50 is contacted with the second material layer 20. The fifth material layer 50 is made of cotton fibers. In this embodiment, when the fifth material layer 50 has better hydrophilic performance than the first hydrophilic portion 221 and the second hydrophilic portion 222 of the second material layer 20, the effect of the present invention is better. In each design mentioned above, each fluid under test 4 is inputted from the other direction relative the first material layer 10, and then permeates into the second material layer 20 via each other material layer for color changing reaction for examination.

After the approximate structure of the personal hygiene item 1 is explained, the following statement will further explain the extended design of the discolored portion 24 of the second material layer 20. According to the statement mentioned in the first embodiment, the first discolored portion 241 or the second discolored portion 242 can be a cotton fabric or paper dipped with reacting matter M2. Additionally, for various different kinds of fluid under test 4, the reacting matter M2 of the present invention can be a nitrite sensing reagent, a glucose sensing reagent, a human serum albumin (HSA) sensing reagent, a wide use reagent, a bilirubin sensing reagent, an urobilinogen sensing reagent, or any kinds of solids or fluids which are able to contact with the corresponding chemical matter of the fluid under test 4 for color changing reaction.

Besides, the reacting matter can be covered by a colloid M1 outside for forming a mixed slurry. The mixed slurry indicated herein is referred to a common state of the reacting matter and the colloid. If needed, the term of "mixed slurry" also can be construed as "the state after solidification". By covering the reacting matter M2 with the colloid M1, the area of the reacting matter M2 contacting with air can be reduced to prolong the storage period of the reacting matter M2. In practical application, the fluid under test 4 can get into the colloid M1 to react with the reacting matter M2 for allowing the color of the reacting matter M2 to be changed for examination.

Furthermore, according to the constituent of the colloid M1 and the reacting matter M2 mentioned above, the colloid M1 of the present invention can be a polymer material. More particularly, the polymer material mentioned above can be a water-soluble polyvinyl alcohol (PVA). But the present invention is not limited to the statement mentioned above, and the polymer material also can be replaced by other transparent water-soluble materials.

Besides the colloid M1 and the reacting matter M2 mentioned above, in practical application, users also can add other additives to provide other properties according to the requirement. It is worth to know that the colloid M1 and the reacting matter M2 of the present invention can be presented by various different kinds of methods, which will be explained in the following statement.

Figure 9:
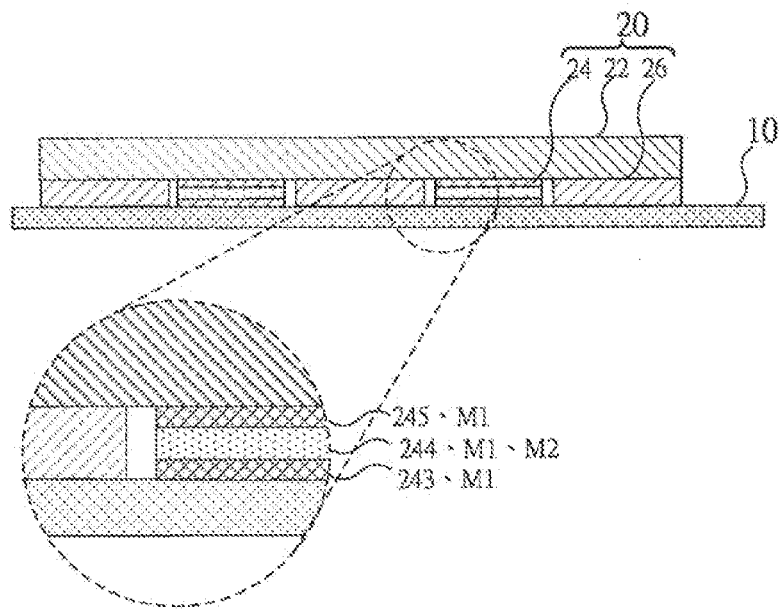

Please refer to FIG. 9. FIG. 9 shows the schematic diagrams of the personal hygiene item according to the ninth embodiment of the present invention. As shown in FIG. 9, it is different from the method in the first embodiment which utilizes cotton fabric or paper to work as the discolored portion 24. As designed in FIG. 8, in this embodiment, the first discolored portion can be approximately divided into three layers, which are the lower colloid layer 243, the testing layer 244, and the upper colloid layer 245 respectively. The testing layer 244 is disposed between the upper colloid layer 245 and the lower colloid layer 243. The lower colloid layer 243 is contacted with the first material layer 10. The lower colloid layer 243 and the upper colloid layer 245 are at least made of the colloid M1 respectively. The testing layer 244 at least comprises the reacting matter, or further comprises the colloid M1 to form the mixed slurry M. In this embodiment, the upper colloid 245 and the lower colloid layer 243 are mainly made of water-soluble polymer material respectively, such as polyvinyl alcohol (PVA).

In practical application, the fluid under test 4 (e.g. urine) can be inputted via one end disposed on the upper colloid 245 and contacted with the upper colloid 245 of the testing material. The moisture of the fluid under test 4 will melt the upper colloid 245 for allowing the fluid under test 4 to contact with the reacting matter M2 of the testing layer 244 for color changing reaction.

The multiple layers structure mentioned above can be manufactured by the following steps. First of all, preparing a liquid state colloid M1 and a liquid state reacting matter M2 respectively. In this embodiment, the liquid state colloid M1 mentioned above is made of polyvinyl alcohol powder (polymerised degree 70,000~100,000) with predetermined percentage (10~15%) mixed with water to form thick state, wherein the viscosity is about 8,000 to 20,000 CPS. It is worth noting that the consistency degree and the thick degree of the polyvinyl alcohol are not limited to the statement mentioned above. Through adjusting the percentage of the polyvinyl alcohol and the water, the consistency degree and the thick degree can be controlled correspondingly.

Upon the colloid M1 and the reacting matter M2 is prepared, mixing part of colloid M1 with reacting matter M2 to form mixed slurry M, wherein the mixed slurry M comprises reacting matter M2.

In this embodiment, if the fluid under test 4 is nitrite, then the reacting matter M2 is a nitrite sensing reagent (the reacting matter M2 comprises 50 mM sulfanilamide, 330 mM citric acid, and 10 mM N-(1-naphthyl)ethylenediamine)). The nitrite sensing reagent (reacting matter M2) can be mixed with colloid M1 for allowing the nitrite sensing reagent (reacting matter M2) to be comprised in the mixed slurry M with the percentage of 20% to 66%, wherein the synergy is better when the percentage is 29%. In the interval, the user can observe the change of the color obviously without over wasting the materials. The synergy is better when the volumetric molar concentration of the fluid under test 4 comprising nitrite which can be examined is between 0.1 mM to 5 mM, wherein the synergy mentioned above is referred to the synthetic effect of the user's ability of observation and the wasted materials.

Similarly, if the fluid under test 4 is glucose, then the reacting matter M2 is a glucose sensing reagent (the reacting matter M2 comprises 75 U/mL glucose oxidase, 15 U/mL horseradish, peroxidase, and 0.6 M potassium iodide). The glucose sensing reagent (reacting matter M2) can be mixed with colloid M1 for allowing the percentage of the glucose sensing reagent (reacting matter M2) comprised in the mixed slurry M to be between 10% to 50%, wherein the synergy is better when the percentage is 20%. And, the synergy is better when the volumetric molar concentration of the fluid under test 4 comprising glucose which can be examined is between 5 mM to 500 mM, wherein the interpretation is more correct when the volumetric molar concentration is between 5 mM to 50 mM.

In another aspect, if the fluid under test 4 is human serum albumin (HSA), then the reacting matter M2 is a human serum albumin (HSA) sensing reagent (the reacting matter M2 comprises 250 mM citric acid and 3.9 mM tetrabromophenol blue). The human serum albumin (HSA) sensing reagent (the reacting matter M2) can be mixed with the colloid M1 for allowing the percentage of the human serum albumin (HSA) sensing reagent (the reacting matter M2) in the mixed slurry M to be 20% to 50%, wherein the synergy is better when the percentage is 33%. The synergy is better when the volumetric molar concentration of the fluid under test 4 comprising human serum albumin (HSA) which can be examined is between 2 μM to 1000 μM, wherein the interpretation is more correct when the volumetric molar concentration is between 10 μM to 150 μM.

If the fluid under test 4 is bilirubin, then the reacting matter M2 is a bilirubin sensing reagent (the reacting matter M2 comprises 4.9 mM sodium nitrite, 145 mM sulfanilic acid, and 104 mM hydrochloric acid). The bilirubin sensing reagent (reacting matter M2) can be mixed with the colloid M1 for allowing the percentage of the bilirubin sensing reagent (reacting matter M2) in the mixed slurry M to be 10% to 50%, wherein the synergy is better when the percentage is 20%. The volumetric molar concentration of the fluid under test 4 comprising bilirubin which can be examined is between 10 mg/mL to 100 mg/mL, wherein the interpretation is more correct when the volumetric molar concentration is between 25 mg/mL to 50 mg/mL.

If the fluid under test 4 is urobilinogen, then the reacting matter M1 is an urobilinogen sensing reagent (the reacting matter M2 comprises 0.1 M 4-dimethylaminobenzaldehyde and 2.8 M hydrochloric acid). The urobilinogen sensing reagent (reacting matter M2) can be mixed with the colloid M1 for allowing the percentage of the urobilinogen sensing reagent (reacting matter M2) in the mixed slurry M to be 16% to 50%, wherein the synergy is better when the percentage is 33%. The volumetric molar concentration of the fluid under test 4 comprising urobilinogen which can be examined is between 17 μM to 500 μM, wherein the interpretation is more correct when the volumetric molar concentration is between 20 μM to 200 μM.

If the pH value of the fluid under test 4 is going to be tested, the reacting matter M2 used to test the pH value (the reacting matter M2 comprises wide use reagent) can be mixed with the colloid M1 for allowing the percentage of the reacting matter M2 used to test the pH value comprised in the mixed slurry M to be 16% to 50%, wherein the synergy is better when the percentage is 20%. The range of the pH value of the fluid under test 4 which can be tested is between pH 4.0 to pH 10.0.

If the fluid under test 4 is ketone body, then the reacting matter M2 is a ketone body sensing reagent (the reacting matter M2 comprises 3% sodium nitroprusside and 0.2 M glycine). The ketone body sensing reagent (reacting matter M2) can be mixed with the colloid M1 for allowing the percentage of the ketone body sensing reagent (reacting matter M2) in the mixed slurry M to be 20% to 66%, wherein the synergy is better when the percentage is 50%. The volumetric molar concentration of the fluid under test 4 comprising ketone body which can be examined is between 0.5 mM to 200 mM, wherein the interpretation is more correct when the volumetric molar concentration is between 5 mM to 20 mM.

Figure 10:
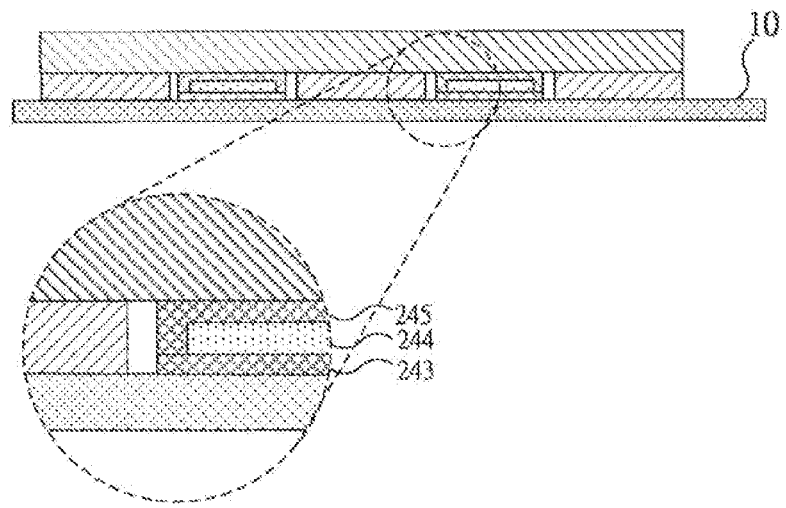

Then, the colloid M1 and the mixed slurry M are disposed inside a forming device respectively, wherein the forming device can be a device corresponding to a impression process, a transfer printing process, an dispenser process, or a screen printing process. After disposing, a lower colloid layer 243 is formed by colloid M1 on the surface of the first material layer 10. And then the testing layer 244 is formed by the mixed slurry M on the lower colloid layer 243. Finally, the upper colloid layer 245 is formed by colloid M1 on the testing layer 244. The structure is shown in the FIG. 9. It is worth to note that the upper colloid layer 245 and the lower colloid layer 243 can be connected on the side of the testing layer 244 for covering the testing layer 244. An example according to the statement mentioned above is shown in the tenth embodiment in the FIG. 10. Upon the multiple layers of structures are formed, and after the moisture in the multiple layers structure is evaporated and the multiple layers of structures are hardened, the process is finished. In the steps of forming each material layer mentioned above, if the material is rarer, the temperature has to be adjusted for allowing the material to be partly hardening or totally hardening. After that, covering the material of the surface over the surface of each layer can acquire a closer structure.

Figure 11:
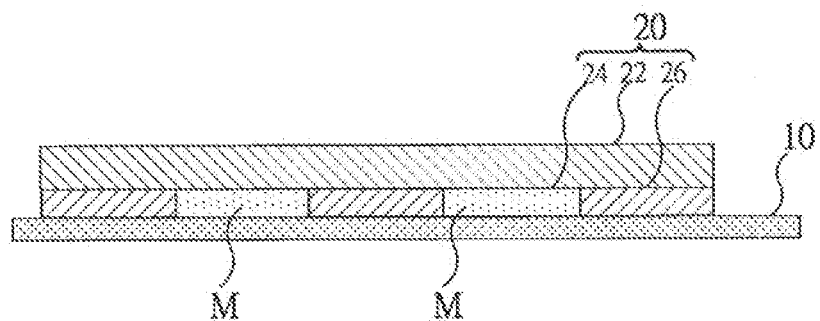

Besides the design of the present invention mentioned above, please also refer to FIG. 11. FIG. 11 shows the schematic diagram of the personal hygiene item according to the eleventh embodiment of the present invention. As shown in the FIG. 11, comparing with other embodiments mentioned above, the difference is that the first discolored portion 241 is a single layer structure in this embodiment. More particularly, the design in this embodiment is different from the designs of the upper colloid layer 245, the testing layer 244, and the lower colloid layer 243 mentioned above. The testing material in this embodiment is formed by spreading the mixed slurry M mentioned over the surface of each testing area Z on each hydrophilic portion 22, which omits the application of the upper colloid layer 245 and the lower colloid layer 243. And the forming method of the structure in this embodiment is similar to the other embodiments mentioned above, so the details will not be given again here.

By the way, in each embodiment mentioned above, users can form the mixed slurry M mentioned above in each testing area Z of the first material layer 10 through dispensers or other methods. It is worth to note that when using a dispenser, each testing area Z is not limited to a single point, and each testing area Z can also be bar-shaped or plane-shaped, according to the requirement of the user.

Figure 12:
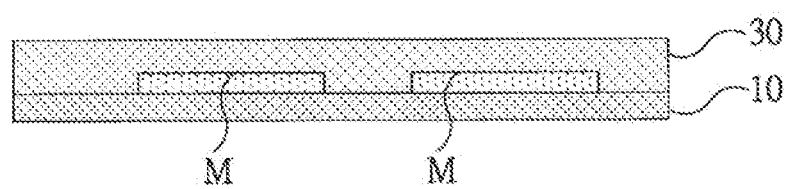
Figure 13:
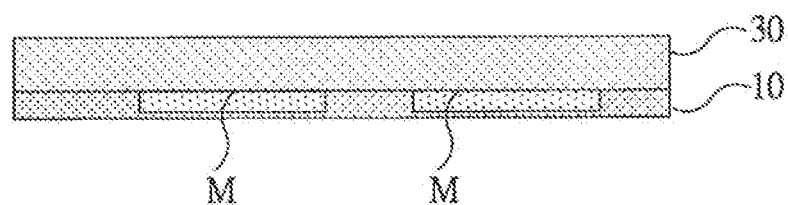

Furthermore, relative to the fifth embodiment and the sixth embodiment, the personal hygiene item of the present invention can also be similar to the drawings in FIG. 12 and FIG. 13, which can use the mixed slurry M mentioned above to form the second material layer 20 as well.

To summarize the statements mentioned above, the priority of the present invention is to provide a personal hygiene item which is able to examine various different kinds of constituents with low cost. In brief, the priority of the present invention is to provide a personal hygiene item which does not have cross contamination and is able to examine various kinds of chemical matters at the same time.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A personal hygiene item, comprising:
   a first material layer, made of a hydrophobic material, adapted to prevent a fluid under test to pass through the first material layer in liquid state, wherein the first material layer is transparent or translucent; and
   a second material layer, disposed on a surface of the first material layer, wherein the second material layer comprises a discolored portion and a hydrophilic portion;
   wherein the discolored portion has better hydrophilic performance than the hydrophilic portion, and the fluid under test permeates into the discolored portion through the hydrophilic portion and is contacted with the discolored portion for color changing reaction, a user can observe the change of the color of the discolored portion via the first material layer for examination.

2. The personal hygiene item of claim 1, wherein the first material layer has at least one indentation, adapted for the second material layer to be laid inside.

3. The personal hygiene item of claim 1 further comprising a third material layer, disposed on the other surface of the second material layer relative to the first material layer and connected with the second material layer, wherein the third material layer is made of at least one hydrophobic material.

4. The personal hygiene item of claim 3, wherein the surface of the third material layer relative to the second material layer has at least one indentation, adapted for the second material layer to be laid inside.

5. The personal hygiene item of claim 3 further comprising a forth material layer, disposed on the other surface of the third material layer relative to the second material layer and connected with the third material layer, wherein the forth material layer is made of a hydrophilic material.

6. The personal hygiene item of claim 1 further comprising a fifth material layer, disposed on the other surface of the second material layer relative to the first material layer and connected with the second material layer, wherein the fifth material layer is made of a hydrophilic material.

7. The personal hygiene item of claim 1, wherein at least one portion of the discolored portion of the second material layer comprises a colloid and a reacting matter, the colloid covers the reacting matter for reducing the area of the reacting matter contacting with air; wherein when the fluid under test is contacted with the discolored portion, the fluid under test gets into the colloid to contact with the reacting matter for color changing reaction and allowing the color of the reacting matter to be changed for examination.

8. The personal hygiene item of claim 1, comprising:
the first material layer; and
the second material layer, disposed on a surface of the first material layer, comprising:
a hydrophilic portion, comprising a first hydrophilic portion and a second hydrophilic portion, the first hydrophilic portion and the second hydrophilic portion have a front surface respectively, the front surface of the first hydrophilic portion and the second hydrophilic portion have a first testing area and a second testing area respectively;
the discolored portion, comprising a first discolored portion and a second discolored portion, wherein the first discolored portion and the second discolored portion are disposed on the surface of the first testing area and the second testing area respectively, wherein the first discolored portion and the second discolored portion have a better hydrophilic performance than the first hydrophilic portion and the second hydrophilic portion respectively; and
a hydrophobic portion, comprising a first hydrophobic portion and a second hydrophobic portion, wherein the first hydrophobic portion and the second hydrophobic portion are disposed on the front surface of the first hydrophilic portion and the second hydrophilic portion respectively, for allowing the first testing area and the second testing area to be exposed from the first material layer respectively, wherein the first hydrophobic portion or the second hydrophobic portion is disposed between the first testing area and the second testing area for isolating the first testing area and the second testing area;
wherein the fluid under test is contacted with the corresponding first discolored portion or the corresponding second discolored portion via the first hydrophilic portion or the second hydrophilic portion of the second material layer for color changing reaction, which allows users to observe the change of the color of the first discolored portion or the second discolored portion via the first material layer for examination.

9. The personal hygiene item of claim 8, wherein the first material layer has at least one indentation, adapted for the second material layer to be laid inside.

10. The personal hygiene item of claim 9, wherein the first material layer has a first indentation and a second indentation, wherein the first indentation is adapted to contain the first hydrophilic portion, the first discolored portion, and the first hydrophobic portion, and the second indentation is adapted to contain the second hydrophilic portion, the second discolored portion, and the second hydrophobic portion.

11. The personal hygiene item of claim 8 further comprising a third material layer, disposed on the other surface of the second material layer relative to the first material layer and connected with the second material layer, wherein the third material layer is made of at least one hydrophobic material.

12. The personal hygiene item of claim 11, wherein the surface of the third material layer relative to the second material layer has at least one indentation, adapted for the second material layer to be laid inside.

13. The personal hygiene item of claim 12, wherein the second material layer has a first indentation and a second indentation, wherein the first indentation is adapted to contain the first hydrophilic portion, the first discolored portion, and the first hydrophobic portion, and the second indentation is adapted to contain the second hydrophilic portion, the second discolored portion, and the second hydrophobic portion.

14. The personal hygiene item of claim 11 further comprising a forth material layer, disposed on the other surface of the third material layer relative to the second material layer and connected with the third material layer, wherein the forth material layer is made of a hydrophilic material.

15. The personal hygiene item of claim 8 further comprising a fifth material layer, disposed on the other surface of the second material layer relative to the first material layer and connected with the second material layer, wherein the fifth material layer is made of a hydrophilic material.

16. The personal hygiene item of claim 8, wherein the first discolored portion and the second discolored portion are made of at least one mixed slurry respectively, wherein the mixed slurry is made of at least one colloid and reacting matter, the colloid covers the reacting matter for reducing the area of the reacting matter contacting with air; wherein when the fluid under test is contacted with the first discolored portion or the second discolored portion, the fluid under test gets into the colloid to contact with the reacting matter for reaction and allowing the color of the reacting matter to be changed for examination.

17. The personal hygiene item of claim 16, wherein the reacting matter is a nitrite sensing reagent, a glucose sensing reagent, a human serum albumin (HSA) a sensing reagent, a pH sensing reagent, a bilirubin sensing reagent, a ketone body sensing reagent, or an urobilinogen sensing reagent; wherein when the reacting matter is a nitrite sensing reagent, the percentage of the reacting matter comprised in the mixed slurry is between 20% to 66%, and the synergy is better when the percentage is 29%, the consistency of the object under test which can be examined by the reacting matter is between 0.1 mM to 5 mM; wherein when the reacting matter is a glucose sensing reagent, the percentage of the reacting matter comprised in the mixed slurry is between 10% to 50%, and the synergy is better when the percentage is 20%, the consistency of the object under test which can be examined by the reacting matter is between 5 mM to 500 mM; wherein when the reacting matter is a human serum albumin (HSA) sensing reagent, the percentage of the reacting matter comprised in the mixed slurry is between 20% to 50%, and the synergy is better when the percentage is 33%, the consistency of the object under test which can be examined by the reacting matter is between 2 μM to 1,000 μM; wherein when the reacting matter is a bilirubin sensing reagent, the percentage of the reacting matter comprised in the mixed slurry is between 10% to 50%, and the synergy is better when the percentage is 20%, the consistency of the object under test which can be examined by the reacting matter is between 10 mg/mL to 100 mg/mL; wherein when the reacting matter is urobilinogen sensing reagent, the percentage of the reacting matter comprised in the mixed slurry is between 16% to 50%, and the synergy is better when the percentage is 33%, the consistency of the object under test which can be examined by the reacting matter is between 17 μM to 500 μM; wherein when the reacting matter is a pH sensing reagent, the percentage of the reacting matter comprised in the mixed slurry is between 16% to 50%, and the synergy is better when the percentage is 20%, the pH value of the object under test which can be examined by the reacting matter is between pH 4.0 to pH 10.0; wherein when the reacting matter is a ketone body sensing reagent, the percentage of the reacting matter comprised in the mixed slurry is between 20% to 66%, and the synergy is better when the percentage is 50%, the consistency of the object under test which can be examined by the reacting matter is between 0.5 mM to 200 mM.

18. The personal hygiene item of claim 16, wherein the first discolored portion and the second discolored portion comprise a lower colloid layer, a testing layer, and an upper colloid layer respectively; the testing layer is disposed between the upper colloid layer and the lower colloid layer; the lower colloid layer is contacted with the first material layer; the lower colloid layer and the upper colloid layer are at least made of the colloid respectively and do not comprise the reacting matter; the testing layer comprises the reacting matter; and the upper colloid layer, the testing layer, and the lower colloid layer of the first discolored portion are formed through piling.

* * * * *